United States Patent [19]
Cross

[11] 4,266,815
[45] May 12, 1981

[54] CONNECTORS

[75] Inventor: David E. Cross, Hythe, England

[73] Assignee: Smiths Industries Limited, London, England

[21] Appl. No.: 54,108

[22] Filed: Jul. 2, 1979

[51] Int. Cl.³ .............................................. F16 25/00
[52] U.S. Cl. .................................... 285/330; 285/332;
    285/354; 285/423; 285/DIG. 16; 285/DIG. 22
[58] Field of Search .................. 285/38, 39, 331, 332,
    285/330, 255, 354, 423, DIG. 16, DIG. 22

[56] References Cited

U.S. PATENT DOCUMENTS

| 2,306,594 | 12/1942 | Cowles | 285/332 |
| 3,616,866 | 11/1971 | Verheul | 285/332 |
| 3,876,234 | 4/1975 | Harms | 285/332 |
| 4,076,285 | 2/1978 | Martinez | 285/332 |

Primary Examiner—Dave W. Arola
Attorney, Agent, or Firm—Pollock, Vande Sande and Priddy

[57] ABSTRACT

A connector for medico-surgical tubing has a plastics body with a male Luer tapered forward portion that is shaped for engagement with a coupling member having a cooperating Luer tapered bore. The body has a rear portion of prismatic shape and square cross-section that is embraced by a square aperture in a rear flange of a locking ring. The locking ring has a cylindrical portion which extends axially of the connector and which has an internal screw thread for engaging cooperating projections on the coupling member. The locking ring is thereby free to slide axially along the prismatic portion of the connector body but is prevented from rotation relative to it. The rear of the Luer tapered portion projects above the surface of the prismatic portion to limit forward displacement of the locking ring.

6 Claims, 5 Drawing Figures

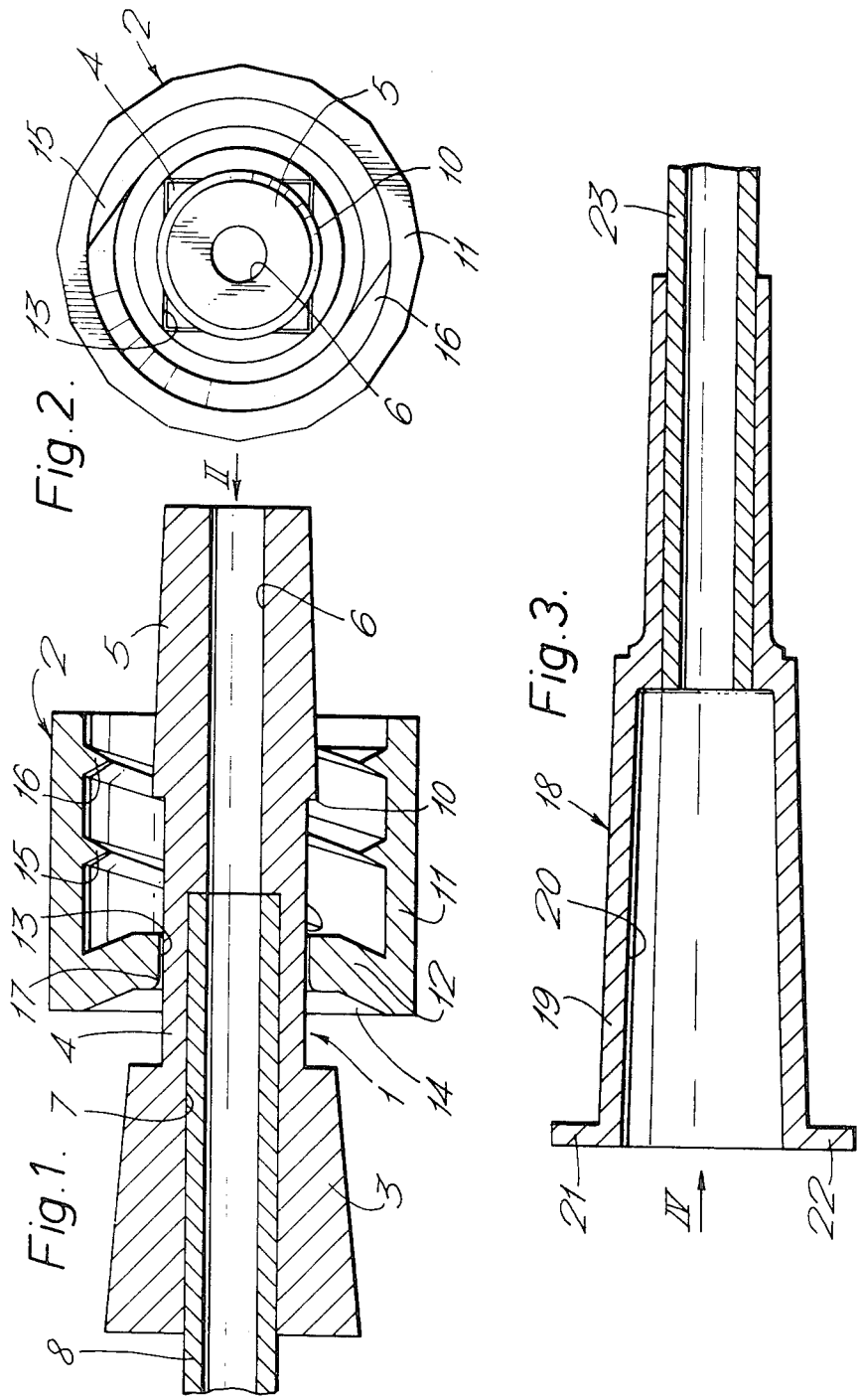

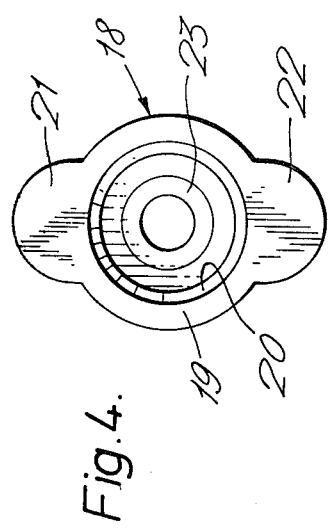
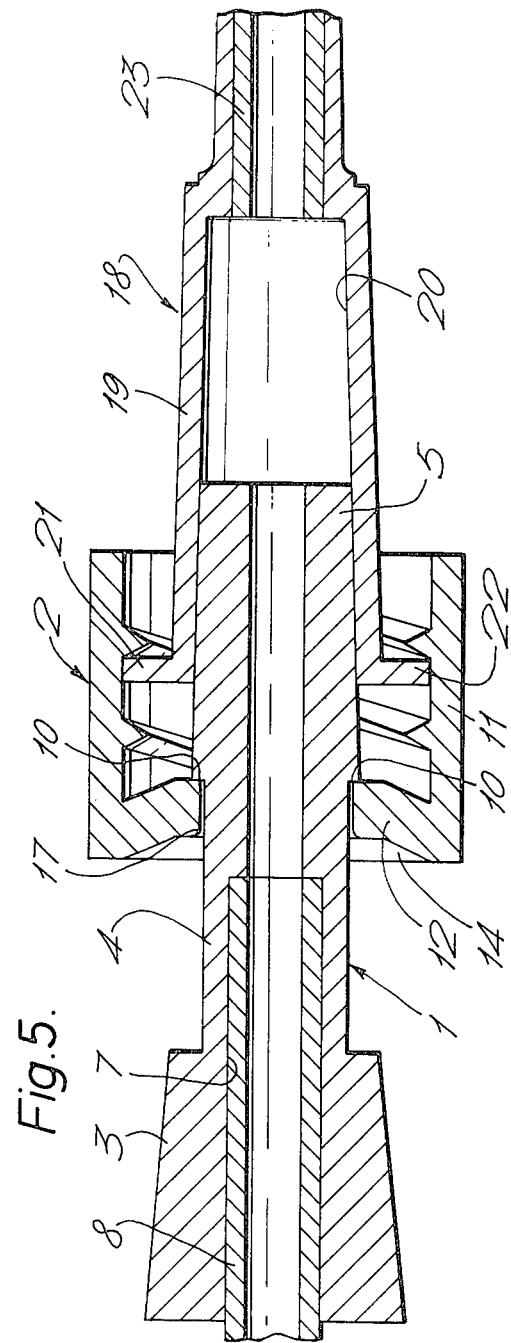

CONNECTORS

BACKGROUND OF THE INVENTION

This invention relates to connectors and in particular to connectors for use in making fluid-tight connections.

More especially, the invention is concerned with connectors for making connection with coupling members provided with a Luer taper.

Luer connectors are commonly used in the medical and surgical fields for coupling together fluid lines or for making connection between, for example, the tip of a syringe, and a fluid line. These connectors are generally of plastics material and are used especially for making connection to medico-surgical tubing, such as catheters, having relatively small diameter internal bores, of the order of 1, 2 or 3 mm.

Luer connections are made by means of a male member having an outer surface which tapers gradually towards its tip, and a female member having a similarly tapered bore of slightly smaller size. When the male member is inserted within the female member the two parts come into frictional engagement with one another to effect a Luer slip fit. Whilst this slip fit is generally reliable it it often desirable to have some form of lock to prevent the male and female members becoming separated inadvertently. In previous arrangements a Luer lock is provided by means of an internally threaded ring rotatably mounted on one member that is adapted to engage suitably shaped projections on the other member.

BRIEF SUMMARY OF THE INVENTION

It is an object of the present invention to provide an improved form of connector.

According to the present invention there is provided a connector having a body with a Luer tapered portion adapted for engagement with a coupling member having a cooperating Luer tapered portion so as thereby to enable a fluid-tight seal to be formed therebetween, wherein the said connector has a locking member mounted thereon that is adapted to engage said coupling member, and wherein said body and said locking member are arranged such as to restrict relative rotation therebetween.

By restricting relative rotation between the locking member and the body, there will be relative rotation between the Luer tapered portion of the connector body and the coupling member when the locking member is twisted to engage or disengage the coupling member. In this way, the seal between the two parts is improved and disengagement is facilitated.

One disadvantage with previous arrangements is that the connector can only be used safely with a coupling member having the correctly shaped projections, since, otherwise the locking member may prevent the connector and the coupling member being fully engaged with one another. In some applications it is necessary to make connection initially with a coupling member provided with suitable locking projections and then to disconnect this member and make connection with a different coupling member that is not provided with such projections, or that is too large to fit within the locking member.

In the present invention the locking member may be mounted for limited axial displacement along the body of the connector.

By mounting the locking member on the connector body in this manner, the risk that the locking member will prevent full engagement with the coupling member is substantially reduced.

The body of the connector may include a portion of prismatic shape and the locking member may comprise a ring having an aperture therethrough that closely embraces the prismatic portion such that the ring can be displaced along the prismatic portion but is restrained from rotation relative to it. The prismatic portion may have a square cross-section.

A Luer connector according to the present invention will now be described, by way of example, with reference to the accompanying drawings.

BRIEF DESCRIPTION OF THE DRAWINGS

FIG. 1 is an enlarged sectional view along the axis of the connector;

FIG. 2 is an end view of the connector from the right-hand of FIG. 1;

FIG. 3 is an enlarged sectional view along the axis of a coupling member for use with the connector of FIGS. 1 and 2;

FIG. 4 is an end view of the coupling member from the left-hand of FIG. 3; and

FIG. 5 shows the coupling member of FIGS. 3 and 4 in position on the connector of FIGS. 1 and 2.

DETAILED DESCRIPTION

With reference to FIGS. 1 and 2, the connector is in two parts, a body portion or shank 1 and a locking ring 2 which is mounted on the shank and which can be moved axially along it to a limited extent.

The shank 1 comprises a rear frusto-conical portion 3, a central portion 4 having a square cross-section, and a forward portion 5 having an outer surface provided with a Luer taper. The entire shank 1 is a one-piece moulding of a plastics material, such as, for example, nylon, and has an axial bore 6 extending therethrough. The bore 6 has a rear, large-diameter portion 7 which extends through the frusto-conical portion 3 and about two thirds the way along the central portion 4 and which receives a connecting line 8. The line 8, which is of a plastics material, may be secured in the large-diameter portion 7 of the bore 6 by means of an adhesive, solvent or by melting or softening the material of the line 8 or the shank 1. The forward part of the bore 6 has a smaller diameter equal to the internal diameter of the line 8 and continues through the central portion 4 to the end of the forward portion 5.

As can be seen from FIG. 2, the diameter of the forward Luer-tapered portion 5 at its rear edge 10 is slightly larger than the thickness of the central portion 4, thereby forming a projection above each of the four faces of the central portion.

The locking ring 2 is also a one-piece moulding of, for example, nylon or other relatively hard plastics material, and comprises a cylindrical sleeve 11 with an outer knurled surface and an inwardly-directed flange 12 at its rear end. The flange 12 is provided with a central square aperture 13 of substantially the same dimensions as the outer surface of the central, square-sectioned portion 4 of the shank 1. The flange 12 is inclined forwardly so as to form a shallow recess 14 at the rear end of the ring 2. The cylindrical inner surface of the sleeve 11 has two threads 15 and 16 which start at points 180° apart and which are adapted to engage with a standard female Luer coupling member which will be described later.

The locking ring 2 is mounted on the shank 1 in the manner shown in FIG. 1 with the aperture 13 in the flange 12 of the ring closely embracing the central square-section portion 4 of the shank. The size of the aperture 13 is such that the ring 2 can be move freely along the length of the central portion 4 of the shank 1 but is prevented from being removed from the forward end of the shank by the projecting edge 10 of the forward tapered portion 5. The flange 12 is also a sufficiently close fit on the central portion 4 to prevent the locking ring 2 being rotated relative to the shank 1. The central portion 4 need not be square in cross-section, but could, for example, be triangular, pentagonal or hexagonal in cross-section. In general, the central portion 4 could be of any prismatic shape providing the aperture 13 in the locking ring 2 is similarly shaped. Alternatively, the central portion 4 could be of oval or elliptical cross-section. In a further alternative arrangement the central portion 4 and the aperture 12 of the ring 2 could be formed with a cooperating key and keyway to prevent relative rotation between them.

Fitting the locking ring 2 on the shank 1 is performed simply by pushing it rearwardly over the forward portion 5, the flange 12 and the shank being sufficiently resilient to allow the ring to pass over the rear edge 10 of the forward portion and to snap onto the central portion 4. The forwardly-inclined shape of the flange 12 enables it to be deformed outwardly somewhat more readily than would otherwise be the case while the rear edge 17 of the aperture 13 is rounded further to ease assembly of the two parts.

The connector of FIGS. 1 and 2 is used for making connection to a standard female Luer coupling member of the kind shown in FIGS. 3 and 4. The female coupling member 18, which is a one-piece moulding of plastics material, has a cylindrical body portion 19 which has an open rear end that is formed with a frusto-conical Luer tapering bore 20. Two lugs 21 and 22 project radially outwards of the coupling member 18 at its rear end, being located diametrically opposite one another. The coupling member 18 is sealed to a connecting line 23 at its forward end by any suitable means.

The female member 18 is coupled with the connector in the manner shown in FIG. 5. The open rear end of the body portion 19 of the member 18 is pushed rearwardly over the forward tapered portion 5 of the connector as far as it will go. The taper and diameter of the two mating parts are arranged such that female coupling member 18 can be pushed about two thirds the way along the length of the forward portion 5. The inherent resilience of the material of the female coupling member 18 and connector is such that the tapered surfaces of the two parts come into frictional engagement with one another to provide a Luer slip-fit, fluid-tight connection.

The connector is locked with the coupling member 18, and the seal between the two parts is improved, by means of the locking ring 2. The locking ring 2 is slid forwardly on the central portion 4 of the shank 1 until the forward, open end of the ring abuts the lugs 21 and 22 on the coupling member 18. The ring 2 is then twisted to engage the lugs 20 and 21 in the threads 15 and 16 and at the same time to screw the ring 2 forwardly until the forward edge of the flange 12 engages the projecting edge 10. Further rotation of the ring 2 draws the female coupling member 18 rearwardly onto the forward portion 5 of the connector. Since the locking ring 2 is not free to rotate on the shank 1, rotation of the ring will also cause rotation of the shank. In this way, as the locking ring 2 is screwed into engagement with the female coupling member 18 the forward portion 5 is simultaneously twisted in the bore 20 of the coupling member thereby ensuring a good seal between the two parts.

To uncouple the connector from the female coupling member 18 the locking ring 2 is twisted in the opposite sense, thereby twisting the tapered forward portion 5 of the connector in the bore 20 of the female coupling member 18. This twisting action effectively breaks the engagement between the male tapered portion 5 and the tapered bore 20 and enables the coupling member 18 to be easily separated from the connector once the locking ring 2 is disengaged from the lugs 21 and 22.

One of the advantages of the connector described above is that it may be used to make connection with various different forms of female coupling member providing they have the standard Luer tapered bore. The locking ring 2 may be slid back away from the forward portion 5 so as to enable free access by coupling members with larger outer dimensions. Connection with the female coupling member is, in this way, made solely by means of the Luer slip-fit and without using the ring 2 to lock the coupling member in position. Without the provision for sliding back the locking ring 2 there is a danger that it might prevent the coupling member being fully engaged with the connector and hence prevent a fluid-tight seal being formed with the coupling member.

Another advantage of the connector described above is that the two parts, namely the shank 1 and the locking ring 2, can each be readily formed as onepiece mouldings and that they can be easily assembled to complete the connector by simply pushing the locking ring over the shank.

I claim:

1. A medico-surgical connector assembly comprising a connector portion and a coupling member, said connector portion having a body with a Luer-tapered portion of plastic material and a locking ring having an aperture therethrough that embraces said body, said body and said aperture being shaped to prevent relative rotation of said locking ring on said body, said coupling member being formed with a plastic Luer-tapered portion shaped for fluid tight cooperating Luer engagement with the said Luer-tapered portion of said connector portion, said coupling member being formed with projections on its outer surface that are shaped to engage with means on the inner surface of said locking ring so that said coupling member can be retained in a fluid-tight seal with said connector portion by said ring, and said body being shaped to permit limited axial displacement of said ring along said body sufficient to enable fluid tight engagement of said cooperating Luer-tapered portions without engagement of the means on the inner surface of said ring with the projections on said coupling member.

2. A medico-surgical connector assembly according to claim 1 wherein the means on the inner surface of said locking ring is a screw thread shaped to engage said projections on said coupling member.

3. A medico-surgical connector assembly according to claim 1 wherein said body includes a portion of prismatic shape and wherein the said aperture in said locking ring closely embraces said portion of prismatic shape.

4. A medico-surgical connector according to claim 3 wherein said prismatic portion is of square cross-section.

5. A medico-surgical connector assembly according to claim 1 wherein the said body includes a portion to the rear of said Luer tapered portion that is embraced by said locking ring and wherein the rear of said Luer tapered portion projects above the surface of a part at least of said portion embraced by said ring so as thereby to limit forward axial displacement of said ring.

6. A medico-surgical connector assembly according to claim 5 wherein said locking ring has a radial flange portion, said aperture being provided in said flange portion, and wherein said flange portion is recessed axially of said connector portion.

* * * * *

UNITED STATES PATENT AND TRADEMARK OFFICE
CERTIFICATE OF CORRECTION

PATENT NO. : 4,266,815
DATED : May 12, 1981
INVENTOR(S) : David E. Cross

It is certified that error appears in the above-identified patent and that said Letters Patent are hereby corrected as shown below:

On the title page add the following:
-- [30] Foreign Application Priority data
July 3, 1978 [GB] United Kingdom 28614/78 --.

Signed and Sealed this

Eighth Day of September 1981

[SEAL]

*Attest:*

GERALD J. MOSSINGHOFF

*Attesting Officer*  *Commissioner of Patents and Trademarks*